US009351752B2

(12) United States Patent
Slavin

(10) Patent No.: US 9,351,752 B2
(45) Date of Patent: May 31, 2016

(54) INSERTION TOOL FOR A SPINAL CORD STIMULATION ELECTRODE

(75) Inventor: Konstantin V. Slavin, Oak Park, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 183 days.

(21) Appl. No.: 13/461,852

(22) Filed: May 2, 2012

(65) Prior Publication Data
US 2012/0283744 A1 Nov. 8, 2012

Related U.S. Application Data

(60) Provisional application No. 61/481,343, filed on May 2, 2011.

(51) Int. Cl.
A61B 17/00 (2006.01)
A61B 17/30 (2006.01)
A61N 1/05 (2006.01)

(52) U.S. Cl.
CPC ....... *A61B 17/30* (2013.01); *A61B 2017/00261* (2013.01); *A61B 2017/00738* (2013.01); *A61N 1/0553* (2013.01)

(58) Field of Classification Search
CPC ...... A61B 17/30; A61B 17/28; A61B 17/282; A61B 2017/00261; A61B 2017/00738
USPC .................................. 606/205, 210, 129, 142
See application file for complete search history.

(56) References Cited

U.S. PATENT DOCUMENTS

| 1,657,497 | A | * | 1/1928 | Cichon | 294/99.2 |
|---|---|---|---|---|---|
| 3,489,151 | A | * | 1/1970 | Eller | 606/106 |
| 4,478,221 | A | * | 10/1984 | Heiss | 606/145 |
| 4,761,028 | A | * | 8/1988 | Dulebohn | 294/99.2 |
| 4,873,979 | A | * | 10/1989 | Hanna | 606/166 |
| 4,976,718 | A | * | 12/1990 | Daniell | 606/131 |
| 5,603,712 | A | * | 2/1997 | Koranda et al. | 606/51 |
| 5,693,057 | A | * | 12/1997 | Dusek | 606/107 |
| 6,146,139 | A | * | 11/2000 | Harrison, III | 433/159 |
| 6,592,583 | B2 | * | 7/2003 | Hirano et al. | 606/52 |
| 8,147,512 | B1 | * | 4/2012 | Puskas et al. | 606/210 |
| 2002/0094507 | A1 | * | 7/2002 | Feuer | 433/162 |
| 2005/0070955 | A1 | * | 3/2005 | Young | 606/210 |
| 2006/0253124 | A1 | * | 11/2006 | Greenberg et al. | 606/129 |
| 2012/0006793 | A1 | | 1/2012 | Swanson | |
| 2012/0197265 | A1 | * | 8/2012 | Sieber et al. | 606/129 |

OTHER PUBLICATIONS

Levy et al., "Incidence and Avoidance of Neurologic Complications with Paddle Type Spinal Cord Stimulation Leads," Neuromodulation, 2011, vol. 14, pp. 412-422.

* cited by examiner

Primary Examiner — Julie A Szpira
(74) Attorney, Agent, or Firm — Michael Best & Friedrich LLP

(57) ABSTRACT

The present invention is directed to an insertion tool for a spinal cord stimulation electrode. The insertion tool comprises a first leg and a second leg coupled to the first leg. The first and second legs are separable for placement around the electrode and resiliently return to a clamped position. Each of the first and second legs generally defines a respective longitudinal axis. Each of the first and second legs defines a blade portion offset from the respective longitudinal axis for clamping the electrode.

14 Claims, 5 Drawing Sheets

INSERTION TOOL FOR A SPINAL CORD STIMULATION ELECTRODE

CROSS-REFERENCE TO RELATED APPLICATIONS

This application claims the benefit of priority to U.S. Provisional Patent Application No. 61/481,343, filed May 2, 2011, the content of which is incorporated herein by reference in its entirety.

FIELD OF THE INVENTION

The present disclosure relates to the development and use of insertion tools for spinal cord stimulation electrodes.

BACKGROUND OF THE INVENTION

A laminectomy is a surgery that removes a portion of the vertebral bone to relieve back pain. It is frequently performed on patients who suffer severe pain due to herniated disks, when more conservative medical treatments have failed. In operation, one or more electrodes or leads are positioned in the cervical spinal region of a patient. For example, the electrode is inserted at a vertebral position into an epidural space, i.e., adjacent or behind the spinal cord. The electrode is then advanced along the epidural space, until it reaches a desired position relative to the cervical segments of the spinal cord. An electrical impulse generator is operatively coupled to the electrode, and delivers an electrical signal to the electrode, thereby stimulating the spinal cord and relieving chronic back pain.

The electrode used in spinal cord stimulation typically resembles a paddle that is generally rectangular when viewed from above. To insert and advance this paddle-type electrode, surgeons typically use straight or bayonet-type forceps. Surgeons must suitably grip the edges of the electrode to ensure its stability. An excessive gripping force, however, tends to bend the electrode in a U-shape. A bent electrode may result in increased pressure on the spinal cord during insertion, and potentially increase the risk of spinal cord injury. Thus, there has developed a need for a tool that can make inserting a paddle-type electrode in laminectomy efficient and surgeon-friendly.

SUMMARY OF THE INVENTION

The present disclosure is directed to an insertion tool for a spinal cord stimulation electrode, the insertion tool comprising a first leg and a second leg coupled to the first leg. The first and second legs are separable for placement around the electrode and resiliently return to a clamped position. Each of the first and second legs generally defines a respective longitudinal axis. Each of the first and second legs defines a blade portion offset from the respective longitudinal axis for clamping the electrode.

The present disclosure is also directed to an insertion tool for a spinal cord stimulation electrode, wherein the offset blade portions are so dimensioned as to facilitate inserting the electrode into an epidural space and advancing the electrode along the epidural space. Each of the offset blade portions includes an electrode-receiving channel formed therein.

The invention is also directed to an insertion tool for a spinal cord stimulation electrode, wherein each of the offset blade portions includes an electrode-receiving channel formed therein. Each of the first and second legs includes a respective intermediate angled portion.

Other aspects of the invention will become apparent by consideration of the detailed description and accompanying drawings.

DETAILED DESCRIPTION

Figure 1:
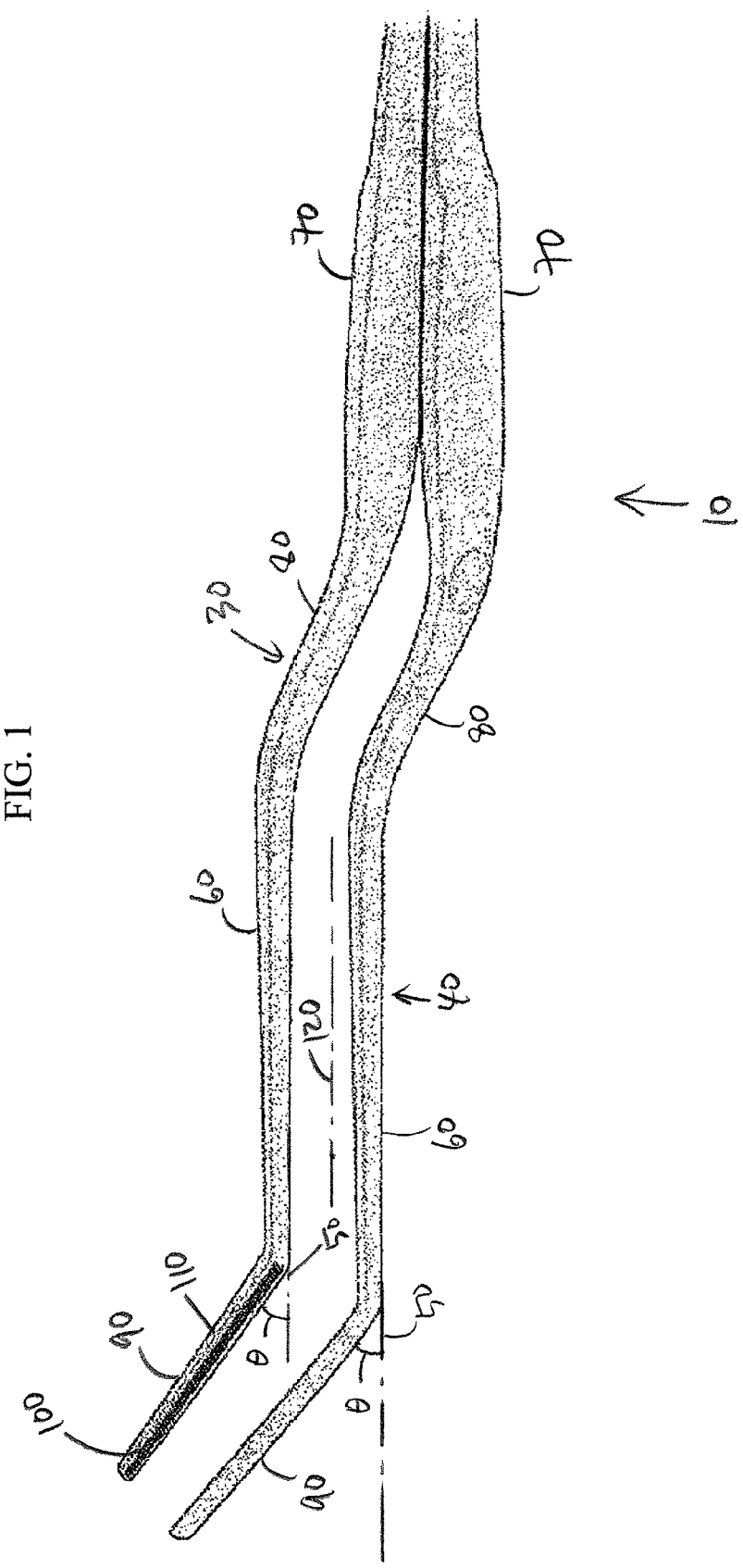
FIG. 1. Perspective view of an insertion tool according to one embodiment of the invention.

For at least the past thirty years, tools such as a Penfield #3 dissector have been used to insert a spinal cord stimulation electrode. The Penfield #3 dissector has a manually engageable handle and a flattened tip formed at an angle to the handle, giving the appearance of a spatula. In operation, the Penfield #3 dissector is advanced under the lamina of the vertebral arch until the tip of the dissector is parallel to the outermost layer of the spinal cord. Inserting the tip past this configuration results in the curved portion of the dissector compressing the spinal cord, which might cause neural injury. Thus, inserting a spinal cord stimulation electrode with the Penfield #3 dissector to a precise position to avoid potential neural injury can be time-consuming and cumbersome.

The spinal cord stimulation electrode is made of a nervous-tissue-compatible dielectric material. This dielectric material has a smooth appearance and is flexible, and therefore can be hard to manipulate. For example, a surgeon may try to grip the electrode with a tool or instrument, yet the electrode may end up slipping, or the surgeon may unintentionally end up flexing the electrode about its midline. Therefore, there has developed a need for a tool that can make gripping and inserting the spinal cord stimulation electrode efficient and surgeon-friendly. Others in the industry, however, have failed to meet this need for at least the past thirty years.

Described herein is an insertion tool for a spinal cord stimulation electrode that enables a surgeon to apply a suitable gripping force to the sides or edges of a paddle-type electrode, to insert the electrode into an epidural space, and to advance the electrode along the epidural space. The insertion tool comprises a first leg and a second leg coupled to the first leg. The first and second legs are separable for placement around the electrode and resiliently return to a clamped position. Each of the first and second legs generally defines a respective longitudinal axis. Each of the first and second legs defines a blade portion offset from the respective longitudinal axis for clamping the electrode. An excessive gripping force can be substantially avoided, thereby avoiding deformations of the electrode. Thus, pressure on the midline spinal structures is decreased, and in turn the risk of spinal cord injury can be decreased.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

2. Insertion Tool

Figure 2:
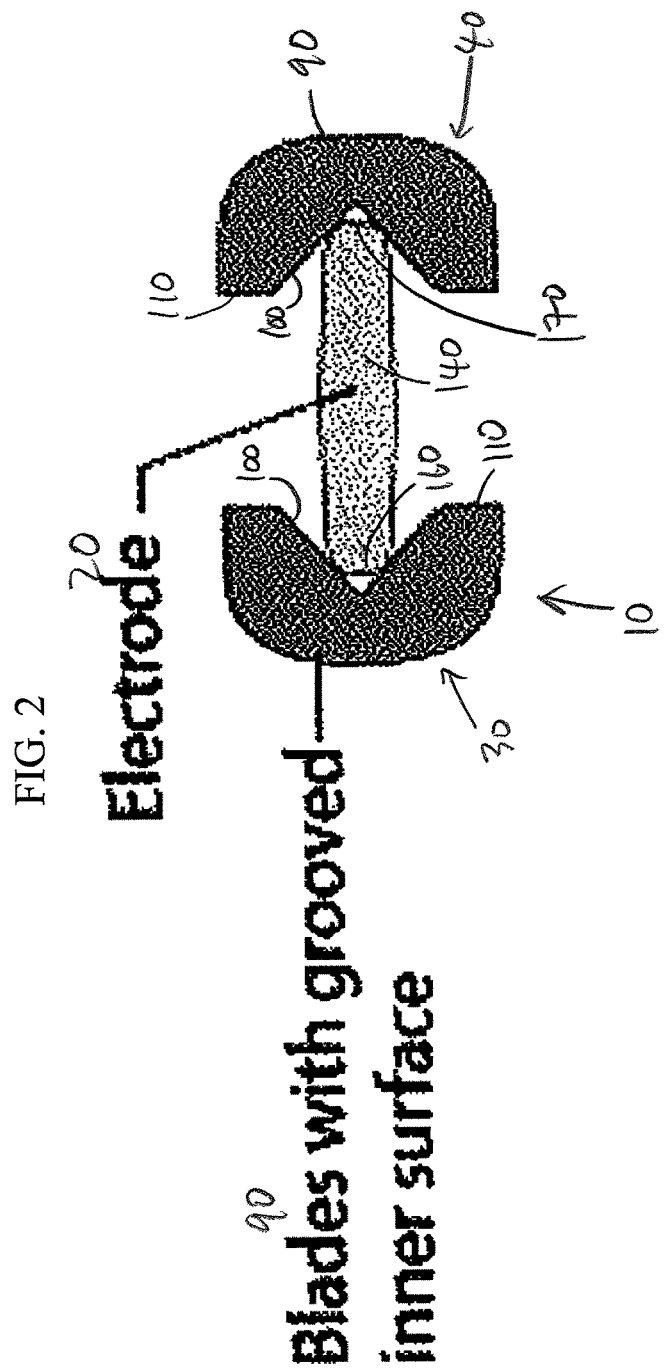
FIG. 2. End view of the insertion tool of FIG. 1.

FIG. 1 illustrates an insertion tool, instrument, forceps, or tweezers 10 for a spinal cord stimulation electrode 20 (not shown in FIG. 1; see FIG. 2). The insertion tool 10 comprises a first leg 30 and a second leg 40 coupled to the first leg 30. Referring also to FIG. 2, the first and second legs 30, 40 are separable for placement around the electrode 20 and resiliently return to a clamped position. For the purposes of the description, the configurations of the first and second legs 30, 40 are generally the same, and will be described with reference to the first leg 30 with the same effect as to the second leg 40. In some embodiments, the insertion tool 10 is formed of metal suitable for surgical tools, e.g., 316L stainless steel. In other embodiments, the insertion tool 10 can be molded or formed from any suitable plastic such as nylon, or can be made in other manners from other materials. In some embodiments, the insertion tool 10 can be sterilized after use, so that it can be used again. Alternatively, the insertion tool 10 can be for a single use, i.e., subsequently disposed.

As illustrated in FIG. 1, the first leg 30 generally defines a longitudinal axis 50. In the illustrated embodiment, the first leg 30 includes end portions 60, 70 which are substantially parallel to each other, and an intermediate angled portion 80 connecting the two end portions 60, 70. Thus, the end portions 60, 70 are offset from each other in elevation, e.g., when the tool 10 is at rest on a desk or other support structure (not shown). In other embodiments, however, the first leg 30 does not include an intermediate angled portion 80, so that the end portions 60, 70 extend in a straight line substantially at the same elevation. In the illustrated embodiment, the cross section of the first leg 30 tapers gradually in thickness in a direction along the longitudinal axis 50 toward the end portion 60 distal from the end portion 70. In other embodiments, however, the first leg 30 may have a substantially uniform thickness in cross section.

The first leg 30 defines a blade portion 90 offset from the longitudinal axis 50 for clamping the electrode 20. The offset blade portion 90 is so dimensioned as to facilitate inserting the electrode 20 into an epidural space and advancing the electrode along the epidural space. In the illustrated embodiment, the offset blade portion 90 is bent away from the respective longitudinal axis 50 at an acute angle θ. In some embodiments, the angle θ is at least about 10°, at least about 20°, at least about 30°, at least about 40°, at least about 50°, at least about 60°, at least about 70°, or at least about 80°. In further embodiments, the angle θ is no more than 80°, no more than 70°, no more than 60°, no more than 50°, no more than 40°, no more than 30°, no more than 20°, or no more than 10°. This includes angles of about 20° to about 80°, about 30° to about 70°, or about 40° to about 60°.

Referring to FIGS. 1 and 2, the offset blade portion 90 includes an electrode-receiving channel 100 formed therein, i.e., on an inner surface 110. In the illustrated embodiment, the electrode-receiving channels 100 are substantially symmetrical from a view along an axis 120 extending midway between the longitudinal axes 50. In other embodiments, however, the electrode-receiving channels 100 may be arranged in other suitable configurations. In the illustrated embodiment, the electrode-receiving channel 100 is a groove that is slightly recessed relative to adjacent portions of the inner surface 110. Although FIG. 1 illustrates the electrode-receiving channel 100 as giving the appearance of a V shape in cross section, in other embodiments, the electrode-receiving channel 100 may assume any geometric form, including, but not limited to, a semi-cylindrical, a regular polyhedral, and an irregular polyhedral shape, derivatives thereof, and combinations thereof. Still other configurations of the tool 10 are possible depending on the usage requirement or other preferences for the particular tool 10, including configurations of the electrode-receiving channel 100 that include other suitable mechanisms to facilitate clamping the electrode 20 tightly, e.g., ribs that are slightly raised relative to adjacent portions of the inner surface 110.

Figure 3:
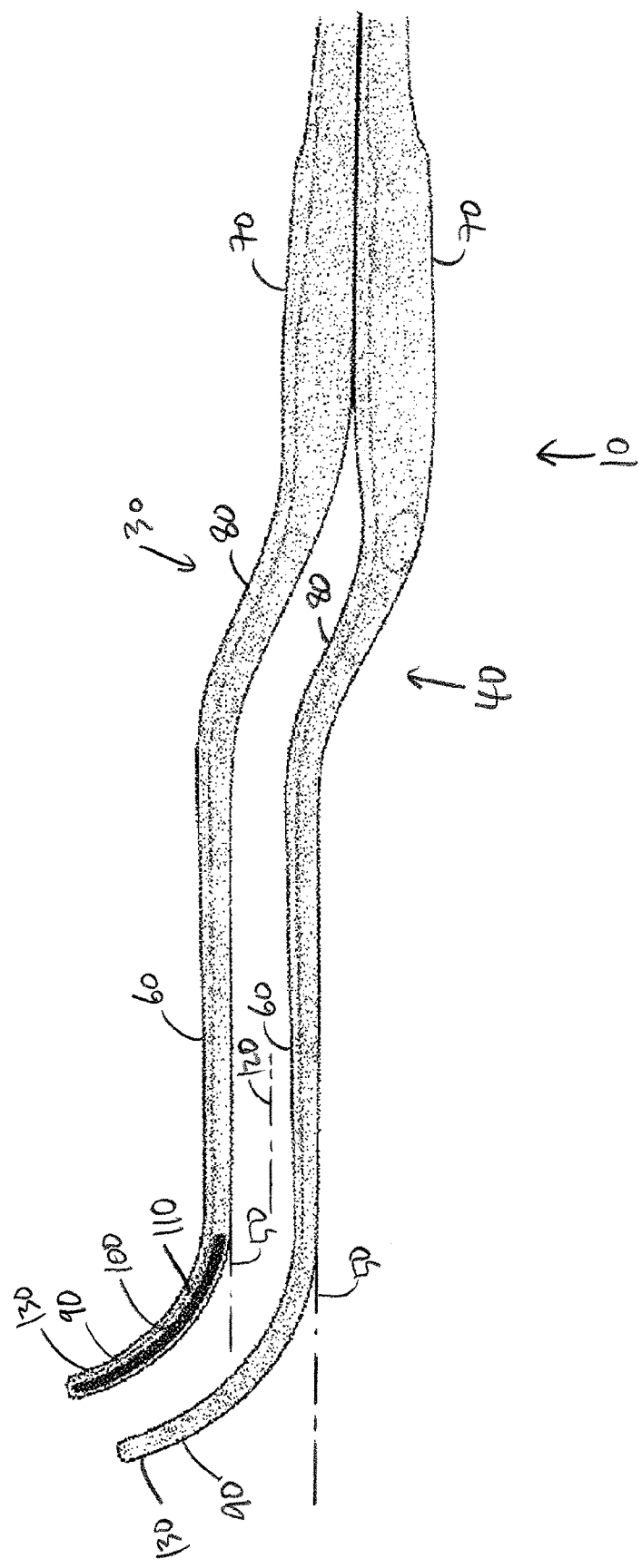
FIG. 3. Perspective view of an insertion tool according to another embodiment of the invention.

FIG. 3 illustrates the insertion tool 10 according to another embodiment of the invention. Like parts are identified using like reference numerals. The offset blade portion 90 in this embodiment includes a curved portion 130. In the illustrated embodiment, the curved portion 130 is a portion of a circle. In other embodiments, the curved portion 130 can be made up of one or more arcuate portions. In operation, at least a part of the electrode 20 may be flexed corresponding to the curved portion 130 of the tool 10 to facilitate gripping and inserting the electrode 20.

3. Method of Using the Insertion Tool

The present disclosure is also directed to a method of using the insertion tool 10. In an operation such as in a laminectomy, a surgeon separates the first and second legs 30, 40 for placement around the electrode 20. The electrode 20 used in laminectomy typically resembles a paddle that is generally rectangular when viewed from above. As such, the electrode 20 includes two short edges 140, 150 at the top and bottom, respectively, and two long edges 160, 170 at the sides. As used herein, the terms "top," "bottom," "front," "rear," "side," and other directional terms are not intended to require any particular orientation, but are instead used for purposes of description only. Once the first and second legs 30, 40 are placed around the side edges 160, 170 of the electrode 20, the first and second legs 30, 40 resiliently return to a clamped position so that the electrode-receiving channels 100 engage the side edges 160, 170 of the electrode 20.

Figure 4:
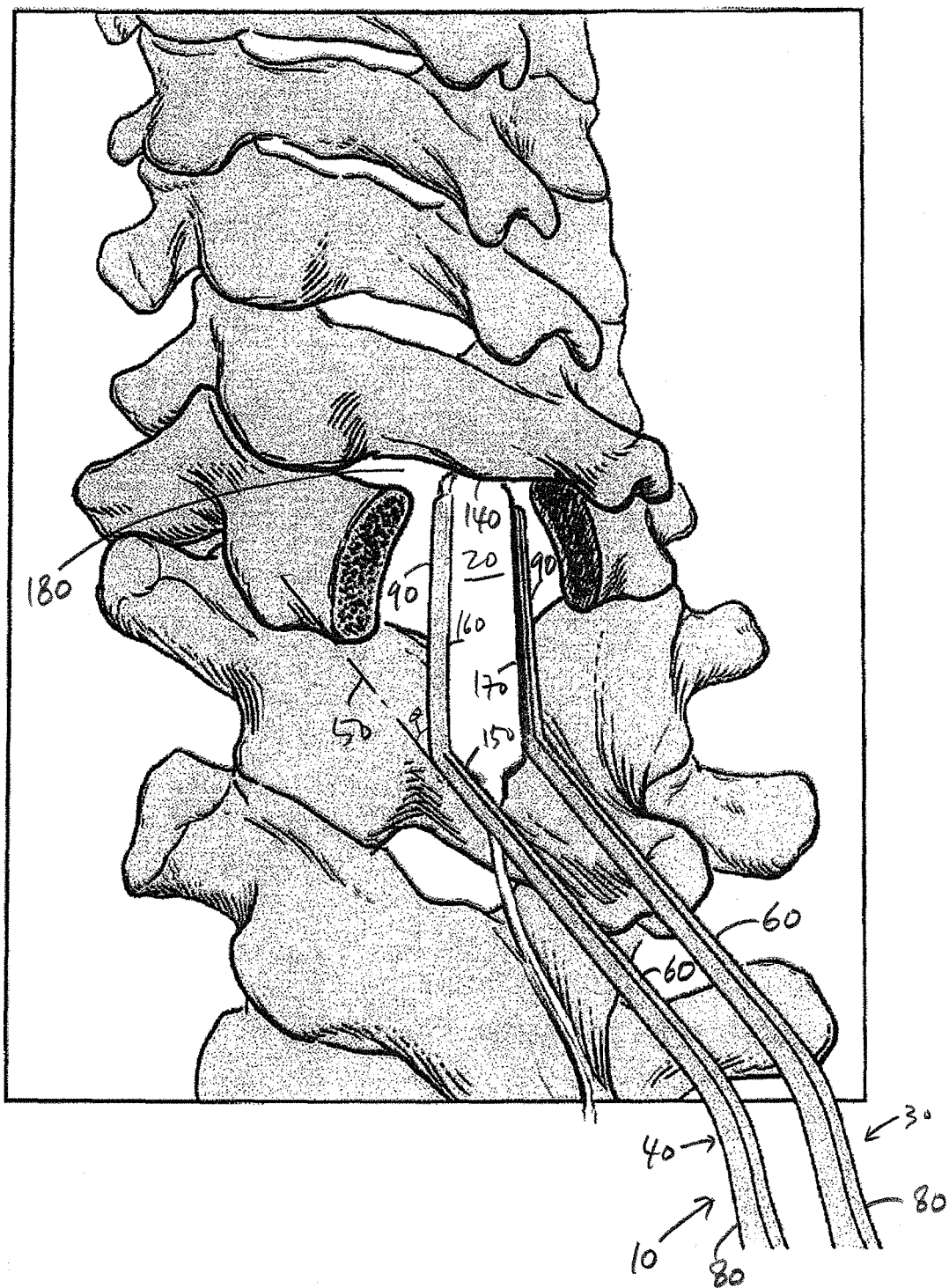
FIG. 4. Schematic illustration of the insertion tool of FIG. 1, illustrating a surgeon inserting a spinal cord stimulation electrode into an epidural space of a patient.
Figure 5:
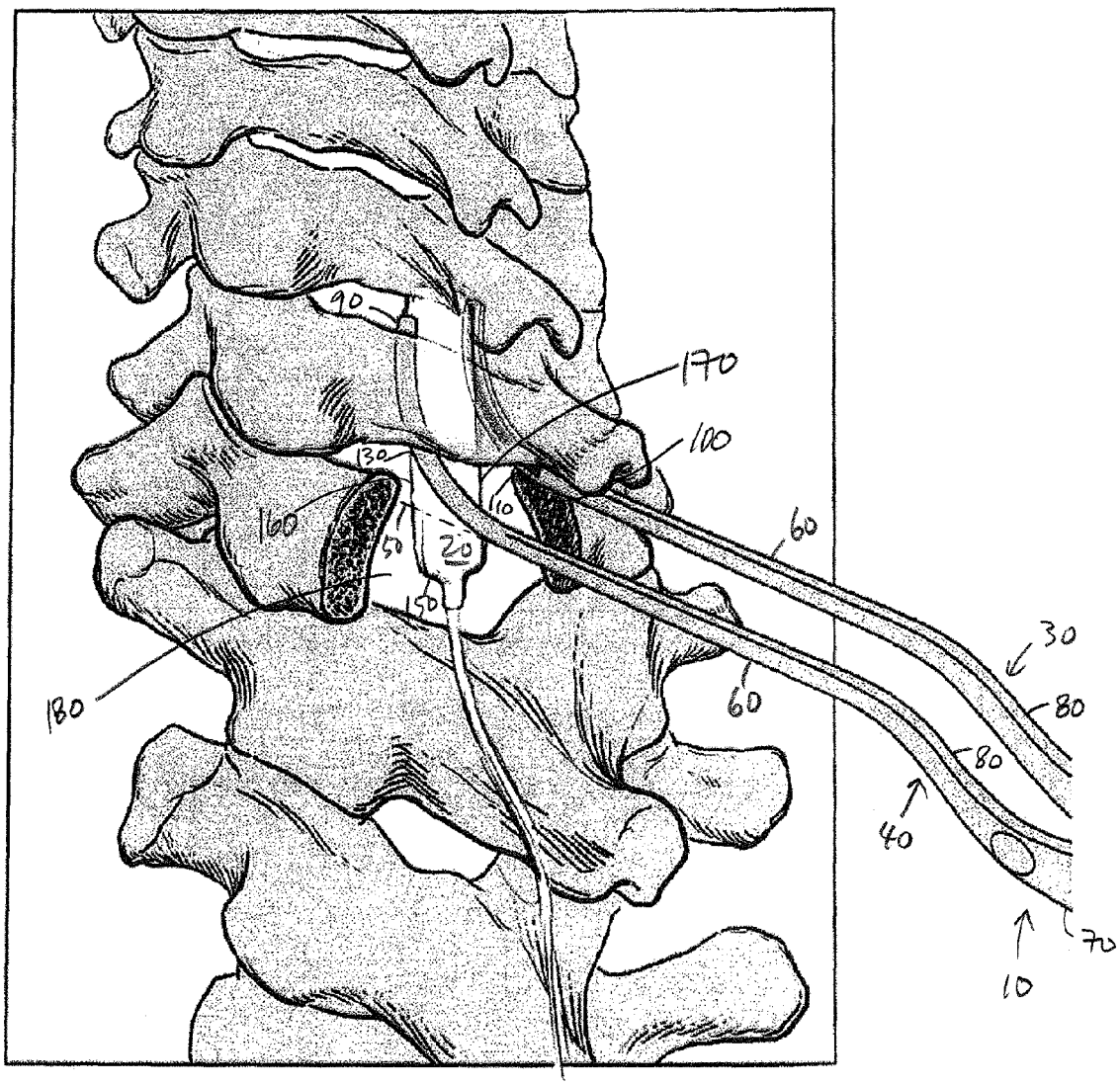
FIG. 5. Schematic illustration of the insertion tool of FIG. 3, illustrating a surgeon advancing a spinal cord stimulation electrode along the epidural space.

Referring to FIG. 4, the surgeon (not shown) inserts the spinal cord stimulation electrode 20 into an epidural space 180 of a patient. Also referring to FIG. 5, the electrode 20 is then advanced a spinal cord stimulation electrode along the epidural space 180. Various techniques such as ultrasound and fluoroscopy may be used to facilitate positioning of the electrode 20. Once the electrode 20 is inserted at the desired level, the first and second legs 30, 40 are separated to release the electrode 20, leaving the electrode 20 in place. An electrical impulse generator (not shown) is operatively coupled to the electrode 20, and delivers an electrical signal to the electrode 20, thereby stimulating the spinal cord and relieving chronic back pain.

Although the invention has been described in detail with reference to certain preferred embodiments, variations and modifications exist within the scope and spirit of one or more independent aspects of the invention as described.

What is claimed is:
1. An insertion tool for a spinal cord stimulation electrode, the insertion tool comprising:
   a first leg;

a second leg coupled to the first leg, the first and second legs being separable for placement around the electrode and resiliently returning to a clamped position, each of the first and second legs generally defining a respective longitudinal axis, each of the first and second legs defining a blade portion offset from the respective longitudinal axis, wherein each of the offset blade portions include an electrode-receiving channel formed therein extending from a proximal-most end of the blade portion to a distal-most end of the blade portion, wherein the electrode receiving channels of each of the first and the second legs are configured to clamp the electrode, wherein the offset blade portions are so dimensioned as to facilitate inserting the electrode into an epidural space and advancing the electrode along the epidural space;

wherein each of the first and second legs includes a respective intermediate angled portion that elevates a first portion of each of the first leg and the second leg above a second portion of each of the first and the second legs, respectively, and wherein the respective blade portions are elevated above both the respective first portions and the second portions of the first and the second legs.

2. The insertion tool of claim 1, wherein the electrode-receiving channels are substantially symmetrical from a view along an axis extending midway between the longitudinal axes.

3. The insertion tool of claim 1, wherein each offset blade portion is bent away from the respective longitudinal axis at an acute angle.

4. The insertion tool of claim 3, wherein the angle ranges between about 20° to about 80°.

5. The insertion tool of claim 1, wherein each offset blade portion includes a curved portion.

6. The insertion tool of claim 1, wherein the cross section of the first and second legs tapers gradually in thickness in a direction along the respective longitudinal axis.

7. The insertion tool of claim 1, wherein an angle between the longitudinal axis of the each of the first and the second legs and the respective blade portions is greater than an angle between the longitudinal axis of each of the first and the second legs and the respective intermediate angled portions.

8. An insertion tool for a spinal cord stimulation electrode, the insertion tool comprising:
a first leg;
a second leg coupled to the first leg, the first and second legs being separable for placement around the electrode and resiliently returning to a clamped position, each of the first and second legs generally defining a respective longitudinal axis, and each of the first and second legs defining a blade portion offset from the respective longitudinal axis, wherein each of the offset blade portions includes an electrode-receiving channel formed therein that extends from a proximal-most end of the blade portion to a distal-most end of the blade portion, wherein the electrode receiving channels of each of the first and the second legs are configured to clamp the electrode, and wherein each of the first and second legs includes a respective intermediate angled portion that elevates a first portion of each of the first leg and the second leg above a second portion of each of the first and the second legs, respectively, and wherein the respective blade portions are elevated above both the respective first portions and the second portions of the first and the second legs.

9. The insertion tool of claim 8, wherein the offset blade portions are so dimensioned as to facilitate inserting the electrode into an epidural space and advancing the electrode along the epidural space.

10. The insertion tool of claim 8, wherein the electrode-receiving channels are substantially symmetrical from a view along an axis extending midway between the longitudinal axes.

11. The insertion tool of claim 8, wherein each offset blade portion is bent away from the respective longitudinal axis at an acute angle.

12. The insertion tool of claim 8, wherein each offset blade portion includes a curved portion.

13. The insertion tool of claim 8, wherein the intermediate angled portions are substantially symmetrical from a view along an axis extending midway between the longitudinal axes.

14. The insertion tool of claim 8, wherein an angle between the longitudinal axis of the each of the first and the second legs and the respective blade portions is greater than an angle between the longitudinal axis of each of the first and the second legs and the respective intermediate angled portions.

\* \* \* \* \*